United States Patent [19]

Louthan

[11] 4,229,588

[45] Oct. 21, 1980

[54] PREPARATION OF DIALKYL DITHIODIALKANOATES

[75] Inventor: Rector P. Louthan, Bartlesville, Okla.

[73] Assignee: Phillips Petroleum Company, Bartlesville, Okla.

[21] Appl. No.: 943,892

[22] Filed: Sep. 19, 1978

[51] Int. Cl.$^2$ .................. C07C 148/00; C07C 149/20
[52] U.S. Cl. ..................................... 560/147; 568/907
[58] Field of Search ................................ 560/147, 154

[56] References Cited

U.S. PATENT DOCUMENTS

| | | | |
|---|---|---|---|
| 2,375,083 | 5/1945 | Cooper | 260/455 |
| 2,530,882 | 11/1950 | Jansen et al. | 560/154 |
| 2,560,421 | 7/1951 | Eby | 260/608 |
| 2,691,000 | 10/1954 | Elliott | 560/154 |
| 3,005,853 | 10/1961 | Wilgus et al. | 260/609 |
| 3,185,620 | 5/1965 | Goodhue et al. | 260/608 |
| 4,052,440 | 10/1977 | Gladstone | 560/154 |

*Primary Examiner*—Vivian Garner

[57] ABSTRACT

A method for obtaining dialkyl dithiodialkanoates in which mercaptoalkyl esters are contacted with a halogen in an inert hydrocarbon solvent to produce a heavy liquid phase of dialkyl dithiodialkanoate and a separate liquid phase of hydrocarbon solvent. These phases are easily separated into the product dialkyl dithiodialkanoate and hydrocarbon solvent which can be recycled without further treatment. In an embodiment of the invention the dialkyl dithiodialkanoate is further contacted with alkylene oxide to neutralize residual acidic by-products in the reaction mixture.

6 Claims, No Drawings

PREPARATION OF DIALKYL DITHIODIALKANOATES

BACKGROUND OF THE INVENTION

This invention relates to a method for preparing dialkyl dithiodialkanoates. In one of its aspects this invention relates to a process for recycling hydrocarbon solvent in a reaction process without purification or other treatment of the solvent. In yet another aspect the invention relates to a method for neutralizing acidic by-products in the production of dialkyl dithiodialkanoates.

In addition to pigments and fillers, commercial paints are composed of several additives which enhance performance and prolong the life of the painted surface. Among these additives are fungicides. Paints are attacked in both the liquid and dry state by various microorganisms (bacteria, fungi). In aqueous paints bacterial fermentation results in odoriferous compounds, loss of viscosity, and popping of can lids due to carbon dioxide formation. Bacteria or fungi most often attack painted surfaces under damp and humid conditions. Some paint pigments such as zinc, copper, lead, and chromium oxides are themselves fungicidal to a certain degree as are alkaline compounds used in paint such as calcium carbonate and barium metaborate. However, in most cases where fungal attack is likely to be severe, additional fungicides sometimes referred to as mildewcides are added. The most widely used paint preservatives are phenylmercuric salts of various organic acids such as phenylmercuric acetate (used in latex water-based paints), phenylmercuric oleate (used in oil-based paints), phenylmercuric propionate (used in both oil and water-based paints), and some chlorinated derivatives. However, because of the environmental hazards associated with mercuric and chlorinated compounds, there exists a need for fungicides based on non-mercuric, non-halogenated products. Among the products being used as fungicides in paints are sulfur-containing organic compounds, such as dialkyl dithiodialkanoates, many of which have gained wide acceptance as control agents in other areas such as agriculture, underground wire installation, bathroom caulking, etc.

It is therefore an object of this invention to provide a method for producing sulfur-containing organic compounds useful as fungicides and mildewcides. It is another object of this invention to provide a method for producing dialkyl dithiodialkanoates. It is still another object of this invention to provide a method for reacting mercaptoalkyl ester with a halogen in which a hydrocarbon solvent can be recycled through the process without further treatment or purification.

Other aspects, objects and various advantages of this invention will become apparent upon reading the specification and appended claims.

STATEMENT OF THE INVENTION

According to this invention a method is provided for preparing dialkyl dithiodialkanoate by contacting mercaptoalkyl ester with a halogen in an inert hydrocarbon solvent thereby producing a first liquid phase of dialkyl dithiodialkanoate and a separate second liquid phase of hydrocarbon solvent and thereafter separating the liquid phases to obtain dialkyl dithiodialkanoate.

In further embodiments of the invention the hydrocarbon solvent from which the dialkyl dithiodialkanoate has been separated can be recycled with fresh mercaptoalkyl ester and halogen to repeat the reaction process without purification or further treatment of the hydrocarbon solvent.

In another embodiment of the invention the dialkyl dithiodialkanoate reaction product is contacted with alkylene oxide to neutralize the reaction product by replacing residual acidic by-products with halohydrin.

The chemical reactions of this invention are represented by the following equations:

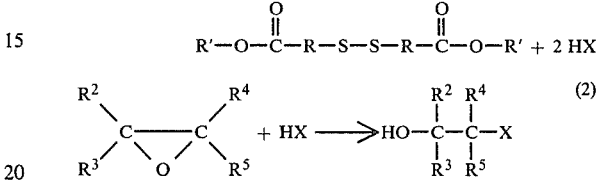

wherein R in equation (1) can be an alkylene radical ranging from 1 to 12 carbon atoms and R' can be an alkyl radical, varying from 1 to 12 carbon atoms. In this disclosure the term alkyl refers also to cycloalkyl and alkylcycloalkyl radicals. X is a halogen in equation (2), $R^2$, $R^3$, $R^3$, $R^5$ can be hydrogen or an alkyl radical ranging from 1 to 6 carbon atoms in any combination.

Representative of typical mercaptoalkyl ester reagents in equation (1) and defined herein are, for example, methylmercaptoacetate, methyl 3-mercaptopropionate, methyl 2-mercaptopropionate, methyl 4-mercaptobutyrate, methyl 3-mercaptobutyrate, methyl 2-mercaptobutyrate, methyl 5-mercaptovalerate, methyl 6-mercaptocaproate, ethyl 2-mercaptoacetate, ethyl 3-mercaptopropionate, propyl 3-mercaptopropionate, isopropyl 3-mercaptopropionate, cyclohexyl 3-mercaptopropionate, and the like.

Representative of typical dialkyl- or dicycloalkyldithiodialkanoate products shown in equation (1) and defined herein are, for example, dimethyl 2,2'-dithiodiacetate, dimethyl 3,3'-dithiodipropionate, dimethyl 2,2'-dithiodipropionate, dimethyl 4,4'-dithiodibutyrate, dimethyl 3,3'-dithiodibutyrate, dimethyl 2,2'-dithiodibutyrate, dimethyl 5,5'-dithiodivalerate, dimethyl 6,6'-dimethyldicaproate, diethyl 2,2'-dithiodipropionate, diisopropyl 3,3'-dithiodipropionate, dicyclohexyl 3,3'-dithiopropionate, and the like.

Coupling agents useful in this invention can be any halogen such as fluorine, chlorine, bromine, or iodine. However, chlorine is the preferred coupling agent. The rate at which the halogen is introduced into the reaction mixture is not critical but the amount of halogen used is critical. The mole ratio of halogen to mercaptoalkyl ester must be controlled between 0.4/1.0 to 0.6/1.0 preferably 0.5/1.0. Less than about 0.4/1.0 mole ratio gives a significant amount of unreacted mercaptoalkyl ester. More than about 0.6/1.0 mole ratio gives a significant amount of sulfenyl halide,

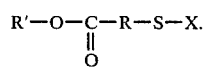

Alkylene oxides can be used as scavenger agents in the present invention to remove residual acidic by-products such as hydrogen chloride from the reaction product and thereby enhance the purity and storage stability of the disulfide diester reaction product. Without this treatment the disulfide diester product is corrosive to carbon steel and, therefore, difficult to store. Representative of typical alkylene oxides shown in equation (2) are, for example, ethylene oxide, propylene oxide, butylene oxide, amylene oxide, and the like. Alkylene oxides having molecular weights below about 150 are preferred since the halohydrin product resulting from the reaction of alkylene oxide and the hydrogen acid has a lower boiling point than the disulfide diester product and, hence, easier to remove in a simple vacuum strip operation for increase in product purity. The alkylene oxides are used in amounts sufficient to neutralize the halogen acids. However, the halohydrin product, if desired, can be left in the product since it usually constitutes less than 0.5 wt. % of the total product.

Inert solvents used in this invention can be saturated aliphatic, cycloaliphatic or substituted aliphatic hydrocarbons. Solvents of this type are satisfactory because they are insoluble in the disulfide diester products of the invention and can be separated therefrom relatively easily by simple phase separation techniques. Such solvents as pentane, hexane, heptane, octane, cyclopentane, methylcyclopentane, cyclohexane, methylcyclohexane, and the like are considered within the scope of this invention. The basic requirement of the solvent is that it possesses very low solubility in the disulfide diester product of the invention.

The present invention can be operated under a slight vacuum, at atmospheric pressure, or under pressure although atmospheric conditions are generally preferred. Although the invention can also be carried out at or below the boiling point of the solvent employed at any convenient reaction temperature at which the reaction can proceed at a reasonable rate without decomposition of reagents or product, reaction temperatures in the ranges of 0°-100° C. are usually found convenient. Generally, it is preferred to conduct the initial reaction of the invention, that is the coupling of the mercapto alkyl ester with a halogen, at or near ambient room temperature and allow the heat of reaction to carry this step to or near the boiling point of the solvent.

At the start of the coupling step the reaction medium is usually homogeneous. Hydrogen halide gas is evolved. After the coupling step is completed, the somewhat cloudy reaction mixture is cooled sufficiently so that two layers are formed. The bottom product layer is removed and subjected to a slight vacuum stripping operation to remove entrained solvent and unreacted mercapto alkyl ester starting material. An alkylene oxide can be added to remove residual halogen acid by-products by formation of halohydrin by-products as defined herein. The alkylene oxide can be added before or after vacuum stripping. The product layer contains essentially pure dialkyl- or dicycloalkyldithiodiester product. The top solvent layer as described herein is returned to the reaction vessel for subsequent reactions without any purification or special treatment. Any unreacted mercapto alkyl ester present is usually found in the heavier product layer.

The following examples serve to illustrate the operability of the present invention. Example I describes a typical preparation of a mercapto alkyl ester starting compound used in the present invention. Example II describes the coupling of a mercapto alkyl ester to a dialkyldithiodiester, phase separation, washing the product layer with aqueous inorganic base and product distillation. Example III is the present invention and describes the complete process. Example IV illustrates the results of recycling unpurified or otherwise treated solvent.

EXAMPLE I

Preparation of Methyl 3-mercapto propionate

Into a one gallon 316 stainless steel reactor fitted with a stirrer, pressure gauge, temperature measuring device and an internal cooling coil was placed 600 milliliters of methanol, 21.6 grams of concentrated amonium hydroxide (28 wt. percent $NH_3$), 12 grams of elemental sulfur and 816 grams (23.94 moles) of hydrogen sulfide. Methyl acrylate (1376 grams, 9.04 moles) was introduced into the stirred reactor over a 45 minute interval. Over the reaction period the temperature of the reaction mixture increased from 23° C. to 53° C. while the pressure decreased from 1650 kPa (239 psig) to 1150 kPa (166 psig). After an additional 30 minutes of stirring, the reactor was vented to release excess hydrogen sulfide and the remaining reaction solution was transferred to a fractionation apparatus.

A total of 5 runs was made as described above. The resulting reaction mixtures were combined prior to fractional distillation.

A fraction (5889 grams) was collected over a boiling range of 87°-93° C. at 50 torr pressure which contained 98.6 wt. percent methyl 3-mercapto propionate as analyzed by GLC (gas liquid chromatography).

EXAMPLE II

Preparation of Dimethyl 3,3'-Dithiodipropionate

To a 2-liter, 3-necked, jacketed glass flask fitted with a stirrer, reflux consenser, a thermowell, a fritted glass bubbler for charging chlorine, and a stopcock in the bottom was charged 1000 milliliters of n-heptane and 240 grams (2.0 moles) of methyl 3-mercapto propionate. Chlorine gas (0.104 moles, 74 grams) was passed into the vigorously stirred reaction mixture from a continuously weighed cylinder over about a 30 minute period. The reaction temperature increased from about 20° C. initially to about 45° C. measured at the end of the chlorination period. In addition, the reaction solution became cloudy during the chlorination.

After the chlorination was complete, the reaction mixture was cooled to about 25° C. by passing tap water through the jacket of the reaction flask. The bottom (product) phase was drained from the flask. The reaction was repeated 4 more times using the top solvent layer from each preceding run for the subsequent runs. About 50 to 60 milliliters of n-heptane was added to each run to make up for possible solvent loses during liquid-to-liquid phase separation. The bottom product layers of all 5 runs were combined and washed with 500 milliliters of 10 wt. percent sodium hydroxide solution and then with 500 milliliters of water. Both the caustic wash and the water wash were basic, which indicated excess caustic was still present. The organic layer was then divided into 2 equal portions. The first portion was stripped by heating to 100° C. at 10 mm (1133 Pa) for 3 to 4 hours and analyzed by GLC equipped with a 6 ft. column containing silicone rubber and programmed between 100°-300° C. at a rate of 25° C./min. and a helium gas flow of 60 cubic centimeters/minutes. The second portion was distilled through a 45 centimeter X 2 centimeter I.D. Vigreaux column to give the desired disulfide diester product boiling at 180°-185° C. at 10 mm (1333 Pa) pressure. Table I shows the results of these experiments. The product obtained by stripping was acidic to pH paper. When the stripped product was treated with 0.25 wt. percent propylene oxide and allowed to stand overnight, the product was neutral to pH paper.

TABLE I

| Dimethyl 3,3'-Dithiodipropionate Washed With Aqueous NaOH | | | | |
|---|---|---|---|---|
| Method of Separation | Purity (% by GLC) | Gardner Color | Yield (Mole %) | pH[a] |
| 1. Vacuum Stripped | 99.9 | 4 | 99.2 | acid |
| 2. Distilled (180°–185° C./10 mm) | 99.8 | 1 | 90.6 | neutral |

[a]Acidity or alkalinity measured by pH paper.

EXAMPLE III

The runs described in Example II were repeated with certain variations in reaction conditions. The aqueous sodium hydroxide wash was omitted since it was shown that the addition of small amounts of alkylene oxide eliminate acidity. Table II shows the results of these additional runs. When the chlorination step was carried out at elevated temperature (Table II,A), the purity of the stripped product was only about 93.7 and the color was darker (Gardner Color, 6) than when distilled (Gardner Color, 3). When the chlorination reaction was conducted at lower temperatures (e.g., 15°–48° C.) but the chlorine to mercapto alkyl ester ratio raised from 0.50/1.0 to 0.52/1.0 (Table II,C), the Gardner Color was significantly darker for the stripped sample than for the distilled sample.

EXAMPLE IV

This example illustrates how the n-heptane solvent (top phase) can be used over again in subsequent chlorination reactions without purification or further treatment. The reaction described in Example II was repeated several times using the method shown in Example III, Table II, Part B wherein chlorination was started at about ambient room temperature and continued as the exotherm for the reaction slowly warmed the contents. After each run the top hydrocarbon layer was removed and used, untreated, in the next run. Additional hydrocarbon was added if needed to bring the total hydrocarbon content to 1000 milliliters. Table III shows the results of re-using untreated hydrocarbon solvent. GLC analysis of the lower phase shows about equal product distribution. Stripping the phase at 100° C./100 gm gave a 96.4 wt. % pure disulfide diester product in a 97.7 mole % yield having a Gardner Color of 2 (Refer Table II,B-1).

Alkyl- or cycloalkyl thioalkanoates dissolved in a hydrocarbon solvent and treated with a halogen between room temperature and the boiling point of the

TABLE II

| Reaction Variations | Purity (% by GLC) | Gardner Color | Yield (Mole %) | pH[a,b] |
|---|---|---|---|---|
| A. Chlorination reaction conducted at 81°–95° C. | | | | |
| 1. Separated by stripping | 93.7 | 6 | 99.2 | acid |
| 2. Separated by distillation | 99.7 | 3 | 88.1 | neutral |
| B. Chlorination started at about 25° C. and allowed to rise to 50°–78° C. through normal exotherm. | | | | |
| 1. Separated by stripping | 96.4 | 2 | 97.7 | acid |
| 2. Separated by distillation | 99.9 | 1 | 89.7 | neutral |
| C. Chlorine to thioalkyl ester ratio increased from 0.50/1.0 to 0.52/1.0 (15°–48° C.). | | | | |
| 1. Separated by stripping | 99.5 | 5 | 97.5 | acid |
| 2. Separated by distillation | 99.5 | 1 | 94.6 | neutral |

[a]Acidity or alkalinity measured by pH paper.
[b]Acidity in all samples reduced to neutral by the addition of 0.25 wt. % propylene oxide.

When the chlorination was started at about 25° C. and the temperature allowed to slowly rise due to the exothermic nature of the chlorination reaction, the Gardner Color was 2 which was only slightly darker than the Gardner Color of the distilled product. Again as in Example II, all stripped samples were acidic to pH paper but were rendered neutral by the addition of 0.25 wt. percent propylene oxide.

solvent couples to give dialkyl- or dicycloalkyl dithiodialkanoates which separate as formed into a heavier liquid phase. The heavy liquid phase is separated, vacuum stripped at 100° C./10 mm to remove dissolved solvent, unreacted starting materials, and acid by-products. The stripped product is treated with an alkylene oxide to react with residual acid which renders the product neutral.

TABLE III

| Run No. | Additional Charge | | Chlorination Condts | | Wt. Lower (Product) Phase Grams | Composition of Lower Phase Area % by GLC | | |
|---|---|---|---|---|---|---|---|---|
| | n-C$_7$ ml | Chlorine Grams | Time (Min.) | Temp. (°C.) | | n-C$_7$ | RSH | RSSR |
| 1 (initial) | 1000 | 73 | 37 | 20–40 | 222.5 | 11.8 | none | 88.0 |
| 2 | 10 | 71 | 57 | 21–36 | 269.7 | 13.1 | 2.8 | 83.3 |
| 3 | 50 | 71 | 33 | 21–40 | 275.5 | 9.8 | 2.6 | 87.4 |
| 4 | 50 | 71 | 78 | 22–35 | 263.0 | 13.9 | 2.5 | 83.3 |

TABLE III-continued

| Run No. | Additional Charge n-C$_7$ ml | Chlorination Condts Chlorine Grams | Time (Min.) | Temp. (°C.) | Wt. Lower (Product) Phase Grams | Composition of Lower Phase Area % by GLC | | |
|---|---|---|---|---|---|---|---|---|
| | | | | | | n-C$_7$ | RSH | RSSR |
| 5 | 30 | 71 | 33 | 21–41 | 273.0 | 11.2 | 4.1 | 84.9 |

I claim:

1. A method for preparing dialkyl dithiodialkanoate comprising:
   (a) contacting in an inert hydrocarbon solvent, a halogen with a mercaptoalkyl ester of the formula $$R'-O-\overset{\overset{O}{\|}}{C}-R-SH$$

wherein R is an alkylene radical having from 1 to 12 carbon atoms and R' is an alkyl radical having from 1 to 12 carbon atoms, the mole ratio of halogen to mercaptoalkyl ester being between 0.4:1 to 0.6:1, to produce (1) a first liquid phase of dialkyl dithiodialkanoate having the formula $$R'-O-\overset{\overset{O}{\|}}{C}-R-S-S-R-\overset{\overset{O}{\|}}{C}-O-R'$$

and (2) a separate, second liquid phase of hydrocarbon solvent, and
   (b) separating liquid phases thereby obtaining (1) dialkyl dithiodialkanoate and (2) hydrocarbon solvent.

2. A method of claim 1 wherein said dialkyl dithiodialkanoate is contacted with alkylene oxide thereby neutralizing residual acidic by-products.

3. A method of claim 1 wherein said hydrocarbon solvent from step (b) is recycled to the contacting of step (a).

4. A method of claim 1 wherein the dialkyl dithiodialkanoate obtained in (b) is subjected to vacuum stripping.

5. A method of claim 4 wherein said dialkyl dithiodialkanoate is contacted with alkylene oxide prior to vacuum stripping.

6. A method of claim 4 wherein said dialkyl dithiodialkanoate is contacted with alkylene oxide subsequent to vacuum stripping.

* * * * *